United States Patent [19]

Targan et al.

[11] Patent Number: 5,750,355
[45] Date of Patent: May 12, 1998

[54] METHODS FOR SELECTIVELY DETECTING PERINUCLEAR ANTI-NEUTROPHIL CYTOPLASMIC ANTIBODY OF ULCERATIVE COLITIS OR PRIMARY SCLEROSING CHOLANGITIS

[75] Inventors: Stephan R. Targan, Los Angeles; Alda Vidrich, Pacific Palisades, both of Calif.

[73] Assignee: Cedars-Sinai Medical Center, Los Angeles, Calif.

[21] Appl. No.: 320,163

[22] Filed: Oct. 7, 1994

Related U.S. Application Data

[63] Continuation of Ser. No. 28,784, Mar. 10, 1993, abandoned.
[51] Int. Cl.$^6$ .................. G01N 33/53; G01N 33/555; G01N 33/567
[52] U.S. Cl. .................. 435/7.24; 435/7.9; 435/188; 435/810; 435/961; 435/962; 435/967; 436/175; 436/519; 436/811; 436/825
[58] Field of Search .................. 435/7.24, 7.9, 435/188, 810, 961, 962, 967; 436/175, 519, 811, 825

[56] References Cited

U.S. PATENT DOCUMENTS 5,238,813  8/1993  Lefkowith .................. 435/7.21
5,292,667  3/1994  Podolsky et al. .................. 436/435

FOREIGN PATENT DOCUMENTS 0094603  11/1983  European Pat. Off. .
9202819  7/1991  WIPO .
9312248  12/1992  WIPO .

OTHER PUBLICATIONS

Cambridge, G., et al., "Anti-neutrophil antibodies in inflammatory bowel disease: prevalence and diagnostic role." *Gut*, 33: 668–674 (1992).

Das, K.M., et al., "The Production and Characterization of Monoclonal Antibodies to A Human Colonic Antigen Associated with Ulcerative Colitis: Cellular Localization of the Antigen by Using the Monoclonal Antibody." *J. Immunology*, 139: 77–84 (1987).

Das, K. M., et al., "A Shared and Unique Epitope(s) on Human Colon, Skin, and Biliary Epithelium Detected by a Monoclonal Antibody." *Gastroenterology*, 98: 464–469 (1990).

Duerr, R. H., et al., "Neutrophil Cytoplasmic Antibodies: A Link Between Primary Sclerosing Cholangitis and Ulcerative Colitis." *Gastroenterology*, 100: 1385–1391 (1991).

Duerr, R. H., et al., "Anti-Neutrophil Cytoplasmic Antibodies in Ulcerative Colitis. Comparison With Other Colitides/Diarrheal Illnesses." *Gastroenterology*, 100: 1590–1596 (1991).

Eggena, M., et al., "Characterization of Ulcerative Colitis Specific pANCA Using Phage Display Technology." *F. Amer. Society of Exper. Biol.*, 8(5): A1010 (1994).

Elsaghier, A., et al., "Antibodies to *Mycobacterium paratuberculosis*-specific protein antigens in Crohn's disease." *Clin. Exp. Immunol.*, 90: 503–508 (1992).

Gross, V. L., et al., "ANCA and associated diseases: immunodiagnostic and pathogenetic aspects." *Clin. Exp Immunol.*, 91: 1–12 (1993).

Halbwachs-Mecarelli, L., et al., "Antineutrophil cytoplasmic antibodies (ANCA) directed against cathepsin G in ulcerative colitis, Crohn's disease and primary sclerosing cholangitis." *Clin. exp. Immunol.*, 90: 79–84 (1992).

Hardarson, S., et al., "Antineutrophil Cytoplasmic Antibody in Inflammatory Bowel and Hepatobiliary Diseases." *Am. J. Clin. Pathol.*, 99: 277–281 (1993).

Kallenberg, C. G. M., et al., "Antineutrophil Cytoplasmic Antibodies: A Still–Growing Class of Autoantibodies in Inflammatory Disorders." *Am. J. Med.*, 93: 675–682 (1992).

King, C. H., et al., "Modulation of Human Neutrophil Effector Functions by Monoclonal Antibodies Against Surface Membrane Molecules of 94,000 and 180,000 Molecular Weight." *Blood*, 67(1): 188–194 (1986).

Lindberg, E., et al., "Antibody (IgG, IgA, and IgM) to baker's yeast (*Saccharomyces cerevisiae*), yeast mannan, gliadin, ovalbumin and betalactoglobulin in monozygotic twins with inflammatory bowel disease." *Gut*, 33: 909–913 (1992).

Lo, S. K., et al., "Antineutrophil antibody: a test for autoimmune primary sclerosing cholangitis in childhood?" *Gut*, 34: 199–202 (1993).

Mulder, A. H. L., et al., "Antineutrophil Antibodies in Inflammatory Bowel Disease Recognize Different Antigens." *Adv. Exp. Med. Biol.*, 336: 519–522 (1993).

Mulder, A. H. L., et al., "Prevalence and Characterization of Neutrophil Cytoplasmic Antibodies in Autoimmune Liver Diseases." *Hepatology*, 17: 411–417 (1993).

O'Mahony, S., et al., "Systemic and mucosal antibodies to klebsiella in patients with ankylosing spondylitis and Crohn's disease." *Ann. Rheum. Dis.*, 51: 1296–1300 (1992).

Rabinovitz, M., et al., "Simultaneous Occurrence of Primary Sclerosing Cholangitis and Autoimmune Chronic Active Hepatitis in a Patient with Ulcerative Colitis." *Dig. Dis. Sci.*, 37(10): 1606–1611 (1992).

Saxon, A., et al., "A distinct subset of antineutrophil cytoplasmic antibodies is associated with inflammatory bowel disease." *J. Allergy Clin. Immunol.*, 86: 202–210 (1990).

(List continued on next page.)

*Primary Examiner*—James C. Housel
*Assistant Examiner*—Ginny Allen Portner
*Attorney, Agent, or Firm*—Campbell & Flores, LLP.

[57] ABSTRACT

The invention is directed to methods and kits for detecting and measuring the presence or absence of perinuclear anti-neutrophil cytoplasmic autoantibody of ulcerative colitis or primary sclerosing cholangitis. The methods and kits of the present invention provide safe and reliable means for diagnosing ulcerative colitis and primary sclerosing cholangitis. The antigens reactive with perinuclear anti-neutrophil cytoplasmic autoantibody of ulcerative colitis and primary sclerosing cholangitis are also provided.

44 Claims, No Drawings

OTHER PUBLICATIONS

Senécal, J., et al., "Autoantibodies to Major and Minor Nuclear Lamins Are Not Restricted to Autoimmune Diseases." *Clin. Immunol. Immunopath.*, 63(2): 115–125 (1992).

Stevens, T. R., et al., "Anti–Endothelial Cell Antibodies in Inflammatory Bowel Disease." *Digestive Dis. and Sci.*, 38: 426–432 (1993).

Wiesner, R. H., et al., "Clinicopathologic Features of the Syndrome of Primary Sclerosing Cholangitis." *Gastroenterology*, 79: 200–206 (1980).

Yang, H., et al., "Ulcerative Colitis: A Genetically Heterogeneous Disorder Defined by Genetic (HLA Class II) and Subclinical (Antineutrophil Cytoplasmic Antibodies) Markers." *J. Clin. Invest.*, 92: 1080–1084 (1993).

Peen, E., et al., "Anti–lactoferrin Antibodies and Other Types of ANCA in Ulcerative Colitis, Primary Sclerosing Cholangitis and Crohn's Disease." *Gut* 34(1): 56–62 (1993).

Bennett, R.M., et al., "Lactoferrin Binds to Neutrophilic Membrane DNA." *British Journal of Haematology* 63(1): 105–117 (1986).

Jack, R M et al, J. Immunol, vol. 137(12), 1986, pp. 3996–4003.

Lamers, M C et al, Eur. J. Immunol., 1981, vol. 11, pp. 757–764.

Contreras, T J et al, Transfusion, vol. 20 (5) 1980, pp. 519–530.

Rao, K M K, J. Gerontol., vol. 41(5), 1986, pp. 561–566.

Strauss, R G et al, J. Reticuloendothelial Soc., vol. 23(6), Mar. 1978, pp. 177–182.

Matul'skaia, L I et al, Vopr. Med. Khim, Jan.–Feb. 1986, vol. 32(1) pp. 32–34. (Abstract, English).

Briggs (1981) J. Histochem. Cytochem. 29, 1128–1136.

Cohen Tervaert (1992) Gastroenterology 102 (3), 1090.

Zauli (1992) Gastroenterology 102 (3), 1088–1089.

Mulder (1993) Adv. Exp. Med. Biol. 336, 545–549 from Presentation on May 28–30, 1992.

METHODS FOR SELECTIVELY DETECTING PERINUCLEAR ANTI-NEUTROPHIL CYTOPLASMIC ANTIBODY OF ULCERATIVE COLITIS OR PRIMARY SCLEROSING CHOLANGITIS

This application is a continuation of application Ser. No. 08/028,784, filed Mar. 10, 1993, now abandoned.

FIELD OF THE INVENTION

The invention relates to methods of detecting and measuring the presence or absence of perinuclear anti-neutrophil cytoplasmic autoantibodies of ulcerative colitis or primary sclerosing cholangitis. More specifically, the methods of the present invention employ DNase treatment of neutrophils in assays such as ELISA and immunofluorescence to elicit the loss of a positive control value when the autoantibody is present.

BACKGROUND OF THE INVENTION

Inflammatory Bowel Disease (IBD) is the collective term used to describe two gastrointestinal disorders, ulcerative colitis (UC) and Crohn's disease (CD). IBD occurs worldwide and is reported to afflict as many as two million people. Onset has been documented at all ages; however, IBD predominately affects young adults.

The three most common presenting symptoms of IED are diarrhea, abdominal pain, and fever. The diarrhea may range from mild to severe and is often accompanied by urgency and frequency. In UC, the diarrhea is usually bloody and may contain mucus and purulent matter as well. Anemia and weight loss are additional common signs of IBD.

A battery of laboratory, radiological, and endoscopic evaluations are combined to derive a diagnosis and to assess the extent and severity of the disease. Nevertheless, differentiating UC from CD, as well as other types of inflammatory conditions of the intestines, such as irritable bowel syndrome, infectious diarrhea, rectal bleeding, radiation colitis, and the like, is difficult. Indeed, depending on the period of follow-up time, in many patients the colitis must be regarded as indeterminate or cannot be definitively diagnosed because of the overlapping features of UC and CD, particularly with CD of the colon.

The selective identification of UC as opposed to CD or other inflammatory conditions of the intestines carries important prognostic and therapeutic implications. For example, when colectomy is indicated, the type of IBD involved determines which surgical options are appropriate. Surgery (total colectomy) does represent a cure in UC, though a dramatic one. In CD, surgery is never curative. Continent procedures such as the ileorectal pull-through (mucosal proctectomy) or the Kock pouch may be desirable in UC, but are contraindicated in CD.

The availability of a diagnostic marker that would readily distinguish UC from CD of the colon and other colitides would represent a major clinical advance. A convenient and reliable blood test which might parallel disease activity or even predict an impending flare of activity would provide a tremendous advantage in the therapeutic management of IBD and aid in the design of more specific treatment modalities.

Although the cause(s) of ulcerative colitis and Crohn's disease is not known, there is general agreement that the immune system is responsible for mediating the tissue damage in these diseases. A wide range of immunologic abnormalities have been reported in these disorders, but none has yet been sufficiently reliable to be of diagnostic value.

A variety of autoantibodies has been observed in UC patients. Most notable among these antibodies have been lymphocytotoxic antibodies and colonic epithelial antibodies. Although these may have genetic and pathophysiologic implications, they have not been useful diagnostically either because of low frequency of occurrence or lack of specificity.

Accordingly, there has existed a need for a convenient and reliable method to distinguish UC from CD of the colon for diagnostic, prognostic and therapeutic purposes.

SUMMARY OF THE INVENTION

The present invention provides methods of detecting and measuring the presence or absence of perinuclear anti-neutrophil cytoplasmic autoantibodies (p-ANCA) of ulcerative colitis (UC) or primary sclerosing cholangitis (PSC) in a sample. More specifically, the presence of p-ANCA of UC or PSC is detected by assaying for the loss of a positive value (i.e., loss of a detectable marker as compared to a control) upon treatment of neutrophils with DNase.

In one embodiment of the present invention, a sample and a detectable secondary antibody are contacted with immobilized, DNAase-treated neutrophil(s) under conditions suitable to form a complex of neutrophil, p-ANCA and detectable secondary antibody. The bound secondary antibody is then separated from unbound secondary antibody, followed by assaying for the presence or absence of p-ANCA containing complex by monitoring for the presence or absence of bound secondary antibody, compared to a control.

The present invention also provides kits containing reagents useful for identifying the presence or absence of p-ANCA of UC or PSC in a sample. The kits include, among other reagents, immobilized neutrophil and a detectable secondary antibody.

The present invention further provides antigens specific to p-ANCA of UC or PSC. Such antigens are insoluble in Triton X-100™.

DETAILED DESCRIPTION OF THE INVENTION

The present invention provides methods and kits for detecting the presence of perinuclear anti-neutrophil cytoplasmic autoantibody (p-ANCA) for ulcerative colitis (UC) or primary sclerosing cholangitis (PSC) in a sample. Inventive methods involve assaying for the loss of a positive value (as compared to a control) upon treatment of neutrophils with DNAase.

As the name indicates, antibodies to cytoplasmic components of the neutrophil are found in the serum of patients with certain chronic inflammatory conditions. By immunofluorescent microscopy, ANCA activity has been divided into two broad categories: cytoplasmic neutrophil staining (c-ANCA) and cytoplasmic staining with perinuclear highlighting (p-ANCA). These distinct staining patterns are obtained with alcohol fixed cytocentrifuged neutrophils and represent an artifact of alcohol fixation. Nevertheless, this alcohol induced localization can serve to distinguish between types of ANCA arising from unique antigens and having different disease associations.

The methods of the present invention exploit the unique staining patterns of UC and PSC as compared to CD and other inflammatory conditions of the intestines, to provide a convenient and reliable method of identifying UC and PSC, eliminating the uncertainty formerly associated with diagnosing and treating IBD.

One aspect of the present invention relates to methods of measuring the presence or absence of p-ANCA of UC or PSC in a sample, comprising:

(a) contacting the sample and a detectable secondary antibody with immobilized neutrophil(s) under conditions suitable to form a complex of neutrophil, p-ANCA and detectable secondary antibody, wherein said immobilized neutrophil is subjected to DNAase under conditions sufficient to cause substantially complete digestion of cellular DNA without significant loss of nuclear or cellular morphology prior to said contacting step, and wherein said secondary antibody has specificity for p-ANCA or the class determining portion of p-ANCA;

(b) separating unbound secondary antibody from the complex;

(c) assaying for the presence or absence of p-ANCA containing complex by measuring the presence or absence of bound secondary antibody, compared to a control, wherein said control is the result of repeating the steps of the present method on a sample from the same source, except that the neutrophil of step (a) is not subjected to DNAase treatment.

In the methods of the present invention, neutrophils are subjected to DNase under conditions sufficient to cause substantially complete digestion of cellular DNA. By the term "complete digestion of cellular DNA" it is meant such digestion of the cellular DNA that the cellular DNA has substantially lost its ability to bind proteins and other cellular materials normally associated with the cellular DNA of the neutrophil. Without being bound by any particular theory, it is presently believed that at least part of the antigens of p-ANCA of UC and PSC are proteins that are either intimately associated with nuclear DNA or with some aspects of nuclear structure.

Conditions sufficient to cause substantially complete digestion of cellular DNA will vary in accordance with the purity and concentration of the DNAase used and include, for example, incubating the immobilized neutrophil in a concentration of DNase of about 2 to 10 units of DNAase per milliliter of a suitable buffer for a time in the range of about 15 minutes to one hour at a temperature in the range of about 22° C. to 40° C.

The assays of the present invention may be forward, reverse or simultaneous as described in U. S. Pat. No. 4,376,110, issued Mar. 8, 1983 to David et al., incorporated herein by reference in its entirety. In the forward assay, each reagent is sequentially contacted with immobilized neutrophil(s). If desired, separation of bound from unbound reagent can be accomplished before the addition of the next reagent. In a reverse assay, all reagents are pre-mixed prior to contacting immobilized neutrophil. A modified method of a reverse assay is described in U.S. Pat. No. 4,778,751 issued Oct. 18, 1988 to El Shami et al., incorporated herein by reference in its entirety. In a simultaneous assay, all reagents are separately but contemporaneously contacted with the immobilized neutrophil. The steps of the presently preferred inventive assay are discussed in further detail below.

As used herein, the term "reagent" refers to any component useful to perform the assays of the present invention, for example, the sample, the primary antibody, the detectible secondary antibody, washing buffers, solutions, and the like.

A sample can be obtained from any biological fluid, for example, whole blood, plasma, or other bodily fluids or tissues having p-ANCA, preferably serum.

The separation steps for the various assay formats described herein, including removing unbound secondary antibody from the complex, can be performed by methods known in the art. When appropriate, a simple washing with a suitable buffer followed by filtration or aspiration is sufficient. If the neutrophil(s) is immobilized on a particulate support, as in the case of microparticles for example, it may be desirable to centrifuge the particulate material, followed by removal of wash liquid. If the neutrophil(s) is immobilized on membranes or filters, applying a vacuum or liquid absorbing member to the opposite side of the membrane or filter allows one to draw the wash liquid through the membrane or filter.

The methods of the present invention are normally carried out at room temperature and 37° C. Because the methods involve the use of proteins, temperatures which would substantially modify the tertiary and quaternary structures of the proteins should be avoided. Accordingly, temperatures suitable for performing the methods of the present invention generally range from about 22° C. to about 38° C.

In a preferred embodiment of the present invention, neutrophil(s) are immobilized on a solid substrate. The solid substrate can be any support useful in immunometric assays. The substrate can be made from natural or synthetic material which is insoluble in water and can be rigid or non-rigid. However, the substrate should not significantly affect the desired activity of the neutrophil(s). Preferred substrates include glass slides, test wells made from polyethylene, polystyrene, nylon, nitrocellulose, glass and the like. Also useful are test tubes, filter paper, filtering devices such as glass membranes, beads, and particulate materials such as agarose, cross-linked dextran and other polysaccharides, and the like.

In accordance with the methods and kits of the present invention, immobilization of neutrophil(s) can be accomplished by any method known in the art. Preferably, a method of immobilization is used that renders the neutrophil (s) permeable to DNAase and the reagents used in the methods and kits of the present invention. For example, neutrophils can be immobilized by fixing them directly to the surface of a test well or glass slide with suitable fixative, such as, for example, methanol, formalin, or the like. Of course, one of skill in the art will appreciate that such fixative should not substantially alter nuclear or cellular morphology of the neutrophil(s).

Neutrophil(s) and secondary antibody appropriate for use in the practice of the present invention will depend upon the origin of the sample assayed. As used herein, the terms "patient," "subject," or "individual" when referring to the origin of the sample to be assayed, means any animal capable of producing p-ANCA of UC or PSC, including for example, humans, non-human primates, rabbits, rats, mice, and the like. Preferably, neutrophil(s) and secondary antibody employed will have specific reactivity for the species from which the sample to be tested is obtained. For example, to assay for p-ANCA of UC or PSC in a sample obtained from a human subject, the neutrophil(s) and the secondary antibody are preferably specific for humans. If multiple antibodies are employed, each antibody is preferably species-specific for its antigen.

Neutrophil(s) useful in the present invention can be obtained from a variety of sources, e.g., the blood of a human, non-human primates, rabbits, rats, mice, and the like, by methods known to those of skill in the art.

The term "secondary antibody" as used herein, refers to any antibody or combination of antibodies or fragments thereof, at least one of which can bind p-ANCA of UC or PSC. For example, a secondary antibody can be an anti-p-ANCA antibody, specific for any epitope of p-ANCA, but preferably not one that would be competitive with neutrophil binding or cause steric hinderance of neutrophil/p-ANCA binding. Alternatively, a secondary antibody can be an anti-IgG preferably having specificity for the class determining portion of p-ANCA.

Secondary antibodies useful in the practice of the present invention can be obtained by techniques well known in the art. Such antibodies can be polyclonal or preferably monoclonal. Polyclonal antibodies can be obtained, for example, by the methods in Ghose et al., *Methods of Enzymology*, Vol. 93, 326–327 (1983). For example, IgG or Fc fragments of IgG can be used as the immunogen to stimulate the production of IgG reactive polyclonal antibodies in the antisera of animals such as rabbits, goats, sheep, rodents, and the like.

Monoclonal antibodies useful in the practice of the present invention can be obtained from a number of commercially available sources. Alternatively, the antibodies can be obtained, for example, by the process described by Milstein and Kohler in *Nature*, 256:495–97 (1975) or as modified by Gerhard, *Monoclonal Antibodies*, 370–371 (Plenum Press, 1980). If a mouse anti-human IgG antibody is desired, a mouse is first injected with an immunogen containing, for example, human IgG or Fc fragments of human IgG. The mouse is subsequently sacrificed and cells taken from its spleen are fused with myeloma cells by methods well known in the art. The resulting hybridomas are screened to isolate clones that secrete a single antibody specie reactive with human IgG.

Preferably, the hybridomas are screened to identify those producing antibodies that are highly specific for the IgG of interest. The monoclonal antibody selected will have an affinity compatible with the desired sensitivity and range for detecting p-ANCA of UC or PSC. The use of such monoclonal antibodies provides a means of obtaining greater sensitivity in the assays of the present invention compared with the use of polyclonal antibodies.

Alternatively, monoclonal antibodies having a high affinity for p-ANCA of UC or PSC can be obtained by the creation of a phage combinatorial library for p-ANCA of UC or PSC and then screening for specificity by a similar process described in Barbas, C. F. et al, *Proceedings of the Nat'l Academy of Science*, 88:7978–82 (1991), set forth herein at Example XIII. Once the IgG fractions having greatest specificity for UC or PSC p-ANCA antigens has been isolated, anti-idiotype antibodies may be raised by methods well known in the art.

Another alternative for increasing the sensitivity of the assay of the present invention is to use a multiple antibody system for the secondary antibody, rather than using a single antibody with enhanced specificity. Thus, the methods of the present invention may be performed using a combination of antibodies as the secondary antibody, wherein at least one secondary antibody of the combination has specificity for p-ANCA or the class determining portion of p-ANCA and at least one secondary antibody of the combination is detectable. For example, UC and PSC may be distinguished from Crohn's disease in a sample of human blood by contacting two aliquots of blood serum from a patient with immobilized untreated or DNAase treated human neutrophil, followed by contacting the resulting antibody-antigen complex with mouse anti-human IgG. The resulting complex is then contacted with goat anti-mouse IgG having a detectable label and washed to remove unbound antibody. The resulting complex is assayed for the presence or absence of a detectable complex, compared to the control (i.e., non-DNAase treated neutrophil). The absence of the labeled goat anti-mouse IgG complexed with DNAase-treated neutrophil(s) indicates that the patient has UC or PSC.

The term "detectible secondary antibody" refers to secondary antibody, as defined above, that can bind p-ANCA of UC or PSC and can be detected or measured by a variety of analytical methods. This term includes antibodies, or fragments thereof, that are directly detectible without attachment of signal generating labels, or those that can be labeled with a signal generating system to permit detection or measurement, such as, for example, any secondary antibody capable of being labeled with a radioisotope, enzyme, chromogenic or fluorogenic substance, a chemiluminescent marker, or the like. Alternatively, a secondary antibody can be made detectible by using biotin-avidin linkage to associate a label with the secondary antibody. In any of the above methods, the reactivity of the secondary antibody with the p-ANCA should not be significantly altered by the presence of the label. When a multi-antibody system is used as the secondary antibody, at least one of the antibodies, combination of antibodies or fragments thereof is capable of binding p-ANCA of UC or PSC, and at least one can readily be detected or measured by suitable analytical methods.

Detectible markers can be bound to the secondary antibody by procedures known to those skilled in the art such as, for example, the chloramine-T procedure for radioactive markers, enzymatically by the lactoperoxidase procedure, by the Bolton-Hunter techniques or any other technique known in the art. These techniques plus others are well known to those of skill in the art and are described, for example, in *Methods in Enzymology*, Volume 70, Part A (Van Vunakis and Langone, editors 1980).

Thus, the secondary antibody can be bound to enzymes such as, for example, horseradish peroxidase, luciferase, malate dehydrogenase, glucose-6-phosphate dehydrogenase, alkaline phosphatase, and the like. The presently preferred enzyme is alkaline phosphatase. Dual channeled catalytic systems may also be used in the methods of the present invention, including, for example, alkaline phosphatase and glucose oxidase using glucose-6-phosphate as the initial substrate. Suitable catalytic systems are described in U.S. Pat No. 4,366,241, issued Dec. 28, 1982 to Tom et al., U.S. Pat. No. 4,740,468, issued Apr. 26, 1988 to Weng et al., U.S. Pat. No. 4,843,000, issued Jun. 27, 1989 to Litman et al., and U.S. Pat. No. 4,849,338, issued Jul. 18, 1989 to Litman et al., all of which are herein incorporated by reference in their entirety.

The procedures for attaching enzymes to various substances are well known in the art. For example, techniques for coupling enzymes to antibodies are described in J. H. Kennedy et al., *Clin. Chim. Acta*, 70:1 (1976). Reagents useful for such coupling include, for example, glutaraldehyde, p-toluene diisocyanate, various carbodiimide reagents, p-benzoquinone m-periodate, N,N'-orthophenylenedimaleimide, and the like.

Alternatively, secondary antibody linked to a detectable enzyme useful for the methods and kits of the present invention may be obtained from a number of commercially available sources, for example, goat F(ab')2 anti-human IgG-alkaline phosphatase may be purchased from Jackson Immuno-Research, located in West Grove, Pa.

Suitable substrates for the above-described enzymatic systems include simple chromogens and fluorogens such as, for example, beta-D-glucose, homovanillic acid, o-dianisidine, bromocresol purple powder, 4-methylumbelliferone, luminol, para-dimethylaminolophine, paramethoxylophine, para-nitrophenyl phosphate, and the like. The presently preferred enzyme substrate is paranitrophenylphosphate.

Secondary antibody may also be rendered detectable by chemically linking it to a fluorogenic compound. Suitable fluorogenic compounds are those that emit light in ultraviolet or visible wavelength subsequent to excitation by light or other energy source. The fluorogens can be employed alone or with a suitable quencher molecule. Presently preferred fluorogens are fluorescein, fluorescein isothiocyanate, tetramethyl-rhodamineisothiocynate, 7-amino-4-methylcoumarin-3-acetic acid and phycoerythrin. The methods of conjugating and using these and other suitable fluorogens have been reported and are described, for example, in *Methods in Enzymology*, Volume 74, Part C, 32105 (Van Vunakis and Langone, Editors 1991).

Alternatively, secondary antibody linked to fluorogen useful for the practice of the present invention may be obtained from a number of commercially available sources, for example, goat F(ab')2 anti-human IgG-FITC available from Tago Immunologicals, Burlingame, Calif.

Depending on the nature of the label or catalytic signal producing system used, a signal can be detected by irradiating the complexed test sample with light and observing the level of fluorescence; by contacting the complexed sample with a substrate which can be catalytically converted by the label to produce a dye, fluorescence or chemiluminescence, in which the formation of dye can be observed visually or in a spectrophotometer; fluorescence can be observed visually or in a fluorometer; or, in the case of chemiluminescence or a radioactive label, by employing a radiation counter such as a gamma counter or gamma emitting markers such as iodine-125. For enzyme-catalyzed systems, when the presently preferred combination of alkaline phosphatase is used as the enzyme and para-nitrophenyl phosphate as the substrate, a color change may be detected visually for a qualitative positive reaction. For a quantitative analysis of the same or similar system, EMAX Microplate Reader (available from Molecular Devices, Menlo Park, Calif.) at 405 nm may be used in accordance with the manufacturer's instructions.

In accordance with the present invention, the presence or absence of p-ANCA of UC or PSC in the sample being tested is determined by contacting a sample with immobilized, DNAase treated neutrophil(s) and secondary antibody, and assaying for the presence or absence of p-ANCA containing complex. The presence or absence of p-ANCA containing complex is determined by monitoring for the presence or absence of bound secondary antibody, compared to a control. P-ANCA is considered present in the test sample if there exists a loss of positive value (bound secondary antibody) in the test sample as compared to the control. The control is the result of repeating the same steps of the inventive method on a sample from the same source, when the immobilized neutrophil has not been subjected to DNAase.

In another aspect of the present invention, kits for measuring the presence of the p-ANCA of UC or PSC in a sample are provided. A kit of the present invention may contain DNAase treated, immobilized neutrophils and a detectable secondary antibody. Alternatively, a kit may contain immobilized neutrophils, DNAase and a detectable secondary antibody. Optionally, depending on the secondary antibody or label used, the kits may contain a signal generating substance to provide or enhance the detection of the p-ANCA of UC or PSC. In addition, other components such as ancillary reagents may be included, for example, stabilizers, buffers, fixatives, and the like. The reagents can be provided as dry powders, usually lyophilized, including excipients, which on dissolution will provide a reagent solution having the appropriate concentrations for performing the methods of the present invention.

A preferred embodiment of the inventive kit includes DNAase and human neutrophils immobilized on a solid substrate, preferably a microtiter plate or beads for detecting or quantitating fluorescence by a cell sorter. To detect the presence of p-ANCA of UC or PSC, the kit preferably includes mouse anti-human IgG, and goat anti-mouse IgG labeled with an enzyme or a fluorogenic substance.

In yet another aspect of the present invention there is provided an isolated antigen of UC. The antigen naturally occurs in neutrophil(s) and is characterized by its insolubility in Triton X-100™ which can be obtained from Fisher, Pittsburgh, Pa., catalogue number BP-151.

In yet another aspect of the present invention there is provided an isolated antigen of PSC. The antigen naturally occurs in neutrophil(s) and is characterized by its insolubility in Triton X-100™.

The invention will now be described in greater detail by reference to the following non-limiting examples.

EXAMPLE I

SEPARATION OF HUMAN PERIPHERAL BLOOD LYMPHOCYTES BY FICOLL-HYPAQUE GRADIENT CENTRIFUGATION

1. Add 31.8 g Ficoll 400 (Pharmacia, Sweden) to 400 ml deionized $H_2O$ in a 500 ml bottle. Shake vigorously until dissolved. Add 100 ml of 50% sodium diatrizoate hypaque (UCLA Pharmacy, Los Angeles, Calif.) and mix.

2. Check specific gravity using a hydrometer. It should be 1.077–1.080.

3. Filter-sterilize Ficoll-hypaque solution through a 0.22 or 0.45 um bottle top filter. The Ficoll-hypaque solution may be stored at 4° C., protected from light.

4. Pour 15 ml Ficoll-hypaque solution into a 50 ml conical centrifuge tube. Carefully overlayer 30 ml heparinized blood.

5. Centrifuge at 1000×g (2000 RPM) for 20 min.

6. Remove interface using a serologic pipet or pasteur pipet and place into 50 ml conical centrifuge tube.

7. Dilute interface layer with at least an equal volume of Hanks' Balanced Salt Solution (HBSS) (Irvine Scientific, Santa Ana, Calif.).

8. Centrifuge at 400×g (1200 RPM) for 5 min.

9. Decant supernatant, resuspend pellet, and add 50 ml HBSS.

10. Repeat twice steps 8 and 9.

11. Resuspend cells in RPMI 1640 (Irvine Scientific, Santa Ana, Calif.) +5% fetal calf serum (GIBCO, Gathersberg, Md).

EXAMPLE II

ISOLATION OF NEUTROPHIL

1. Using a pipet, carefully remove serum and remaining Ficoll-Hypaque from red blood cell pellet resulting from procedure described in Example I.

2. Add 10 ml 6% dextran to 15 milliliters of pellet.

3. Top off with 1× HBSS to 50 ml. Re-suspend pellet.

4. Allow red blood cells to settle, approximately 45 minutes to one hour.

5. Separate supernatant, discard pellet. Top supernatant off with 1× HBSS to 50 ml and centrifuge for 5 minutes at 1800 rpm.

6. Decant supernatant and tap pellet.

Hypotonically lyse remaining red blood cells by adding 9 ml deionized water, swirl, and then add 1 ml 10× HESS and immediately dilute with 1× HBSS to 50 ml.

7. Centrifuge for 5 minutes at 1000 rpm. Discard supernatant and re-suspend pellet in 15 ml 1× HBSS.

EXAMPLE III

IMMOBILIZATION OF NEUTROPHIL(S) ON GLASS SLIDES

1. Count cells in suspension of step 7 of Example II using a microscope and hemacytometer and re-suspend cells in sufficient volume of 1× HBSS to achieve $2.5 \times 10^6$ cells per ml.

2. Use Cytospin $_3$Tm (Shandon, Inc. Pittsburgh, Pa.) at 500 rpm for 5 minutes to apply 0.01 ml of the re-suspended cells to each slide.

3. Fix cells to slide by incubating slides for 10 minutes in sufficient volume of 100% methanol to cover sample. Allow to air dry. The slides may be stored at $-20°$ C.

EXAMPLE IV

DNAase TREATMENT OF NEUTROPHIL(S) IMMOBILIZED ON GLASS SLIDE

Prepare a DNAase solution by combining 3 units of Promega RQ1™ DNAase per ml buffer containing 40 mM of TRIS-HCl (pH 7.9), 10 mM of sodium chloride, 6 mM magnesium chloride and 10 mM calcium chloride. Promega RQ1™ DNAase can be obtained from Promega, of Madison, Wis.

Rinse slides prepared in accordance with Example III with about 100 ml phosphate buffered saline (pH 7.0–7.4) for 5 minutes. Incubate immobilized neutrophils in 0.05 ml of DNAase solution per slide for about 30 minutes at 37° C. Wash the slides three times with about 100–250 ml phosphate buffered saline at room temperature.

EXAMPLE V

IMMUNOFLUORESCENCE ASSAY

1. Add 0.05 ml of a 1:20 dilution of human sera in phosphate buffered saline to slides treated with DNAase in accordance with Example IV and to untreated slides of Example III.

Add 0.05 ml phosphate buffered saline to clean slides as blanks. Incubate for 0.5 to 1.0 hours at room temperature in sufficient humidity to minimize volume loss.

2. Rinse off sera by dipping into a container having 100–250 ml phosphate buffered saline.

Soak slide in phosphate buffered saline for 5 minutes. Blot lightly.

3. Add 0.05 ml goat F(ab')$_2$ anti-human IgG(μ)-FITC, at a 1:1000 antibody:phosphate buffered saline dilution, to each slide. Incubate for 30 minutes at room temperature, in sufficient humidity to minimize volume loss. (Goat F(ab')$_2$ anti-human IgGo-FITC is available from Tago Immunologicals, Burlingame, Calif., catalogue #4200.)

4. Rinse off antibody with 100–250 ml phosphate buffered saline. Soak slides for 5 minutes in 100–250 ml phosphate buffered saline, then allow to air dry.

5. Read fluorescence pattern on fluorescence microscope at 40×.

If desired, any DNA can be stained with propidium iodide stain by rinsing slides well with phosphate buffered saline at room temperature and stain for 10 seconds at room temperature. Wash slide three times with 100–250 ml phosphate buffered saline at room temperature and mount cover slip.

EXAMPLE VI

DNAase SENSITIVITY OF UC p-ANCA SPECIFIC ANTIGEN USING IMMUNOFLUORESCENCE ASSAY DNAase obtained from Promega was used at a working concentration of 3 units/ml. DNAase concentration was optimized by titrating the amount of DNAase added (from 1 to 10 units/ml) and examining the extent of DNA digestion by propidium iodide staining and/or reaction with anti-DNA antisera. Digestion of cytocentrifuged, methanol fixed neutrophils was carried out at 37° C. for 30 minutes with DNAase solubilized in 40 mM Tris-HCl (pH 7.9) buffer containing 10 mM NaCl, 6 mM MgCl$_2$ and 10 mM CaCl$_2$. Virtually all cellular DNA was lost, as indicated by the lack of propidium iodide staining. Also lost was the reaction of an anti-histone positive serum. DNAase reaction carried out as described herein does not significantly alter nuclear or cellular morphology.

Neutrophils treated with trypsin at various concentrations no longer reacted with UC p-ANCA positive sera nor with anti-histone positive serum, indicating that at least part of the p-ANCA reactive antigen is a protein. Similarly, pepsin digestion of neutrophils abolished PSC p-ANCA positive serum reaction, again indicating the proteinaceous character of this antigenic species.

Panels of UC p-ANCA positive and c-ANCA positive patient sera were examined for DNAase sensitivity using cytocentrifuged, methanol fixed slides as described above. Two other types of reactions were noted. Some p-ANCA positive sera lost the perinuclear aspect of the reaction and became cytoplasmic after DNAase treatment, while c-ANCA positive sera generally remained cytoplasmic. Additionally, some sera that were found to have both a perinuclear and cytoplasmic ANCA staining reaction always lost the perinuclear aspect of the reaction after DNAase treatment of neutrophils. These DNAase-induced staining patterns proved to be highly reproducible from experiment to experiment.

These data indicate at least three ANCA reactions are possible in response to DNAase treatment of immobilized neutrophils; 1) a p-ANCA reaction that is abolished, 2) a p-ANCA reaction that becomes cytoplasmic and 3) a c-ANCA reaction that persists. In all of these cases, the DNAase digestion was complete as evidenced by a lack of propidium iodide staining as well as lack of reaction by anti-DNA antibody. Finally, it was also examined whether prior reaction of neutrophils with p-ANCA positive serum would effect the DNAase sensitivity of antigen. The perinuclear reaction is maintained even after DNAase digestion when neutrophils are first treated with the p-ANCA positive serum. This result indicates a protective effect of antibody binding against either physical loss of antigen or loss of epitope recognition.

EXAMPLE VII

IMMOBILIZATION OF NEUTROPHIL(S) ON MICROTITER PLATE

1. Count cells in suspension of step 7 of Example II using a microscope and hemacytometer and re-suspend cells in sufficient volume of 1× HBSS to achieve 2.5×10⁶ cells per ml. Add 0.1 ml per well to a 96-well microtiter Immulon 1™ or Immulon™ plate (available from Dynatech Laboratories of Chantilly, Va.) and let settle for 30–60 minutes.

2. Pull supernatant with 8 channel manifold connected to a vacuum and let plate air dry (approximately 2 hours) or turn upside down on the grate of a laminar flow hood to dry (approximately 10 minutes).

3. Fix cells to well by incubating cells for 10 minutes in 0.1 ml of 100% methanol per well. Discard methanol and let plate air dry. Store at −20° C.

EXAMPLE VIII

DNAase TREATMENT OF NEUTROPHIL(S) IMMOBILIZED ON MICROTITER PLATE

A DNAase solution is prepared by combining 3 units of Promega RQ1™ DNAase per ml buffer containing 40 mM of Tris-HCl (pH 7.9), 10 mM sodium chloride, 6 mM magnesium chloride and 10 mM calcium chloride.

Rinse plates prepared in accordance with Example VII once with 25 ml phosphate buffered saline. Incubate immobilized neutrophils in 0.1 ml of DNAase solution per well for about 30 minutes at 37° C. Wash the wells three times with a total of about 100 ml phosphate buffered saline. Block the wells by adding 0.15 ml of 0.25% bovine serum albumin in phosphate buffered saline (pH 7.4) and allowing to stand at room temperature for about one hour. Discard blocking fluid.

EXAMPLE IX

DNAase-TREATED, FIXED NEUTROPHIL ELISA

1. Add 0.1 ml human sera diluted as desired with phosphate buffered saline containing 0.25% bovine serum albumin to each well of the microtiter plates prepared in accordance with Example VIII and Example VII (i.e., with and without the DNAase treatment). Add 0.01 ml phosphate buffered serum containing 0.25% bovine serum albumin to blank wells. Let stand at room temperature for one hour, in sufficient humidity to minimize volume loss.

2. Aspirate serum. Wash three times with a total of about 100 ml phosphate buffered saline containing 0.02% sodium azide (NaN₃) and 0.05% Tween.

3. Add to each well 0.1 ml of a 1:1000 dilution of alkaline phosphatase-coupled goat antihuman IgG antibody in phosphate buffered saline containing 0.25% bovine serum albumin. Goat F(ab')₂ anti-human IgG(Fc)-alkaline phosphatase may be obtained from Jackson Immuno-Research Laboratories in West Grove, Pa. Incubate for one hour at room temperature in sufficient humidity to minimize volume loss.

4. Wash three times with a total of 100 ml phosphate buffered saline containing 0.02% sodium azide (NaN₃) and 0.05% Tween. Wash three more times with TRIS-NaCl solution containing 0.05M Tris, 0.15M NaCl, and 0.02% sodium azide, pH 7.5.

5. Combine 0.75 g disodium p-nitrophenol phosphate (United States Biochemicals catalogue #19587 or AMRESCO catalogue #P0364) with a Tris buffer containing 75 mM Tris-HCl, 1.5 mM MgCl₂, 0.02% sodium azide, pH 8.6 to form a substrate containing solution. Add 0.01 ml substrate containing solution to each well. Incubate at room temperature for 60 to 90 minutes in sufficient humidity to minimize volume loss, until blank wells reach 0.8 in absorbance.

6. Read plate at 405 nm in an EMAX Microplate Reader (Molecular Devices, Menlo Park, Calif.)

EXAMPLE X

CHANGE IN ANCA BINDING TO DNAase TREATED NEUTROPHILS RELATIVE TO CONTROL UNTREATED CELLS USING DNAase-TREATED, FIXED NEUTROPHIL ELISA In a panel of p-ANCA positive UC sera, the subset found to lose greater than 50% of ANCA binding by ELISA corresponds to those that lost most or all of the p-ANCA staining by immunofluorescent staining. On the other hand, sera showing less than about 50% reduction in ANCA binding by ELISA were found to display a p-ANCA pattern that converted to cytoplasmic staining after DNAase digestion of neutrophils. In this latter group was also found a few sera with a mixture of perinuclear/cytoplasmic staining pattern that retained only the cytoplasmic pattern post DNAase treatment. The one serum displaying a cytoplasmic ANCA staining pattern was found to have increased ANCA binding post DNAase treatment. The majority (4 out of 6) of p-ANCA positive PSC sera lost less than 50% of the ANCA binding after DNAase treatment of neutrophils; in contrast only 5 out of 14 UC p-ANCA positive sera showed such a loss. By immunofluorescent staining these PSC sera were found to display a p-ANCA staining pattern that became cytoplasmic after DNAase treatment.

Thus, the DNAase-treated, fixed neutrophil ELISA may be used to distinguish UC and PSC from CD, as well as other types of inflammatory conditions of the intestines. The unique perinuclear/cytoplasmic staining patterns associated with immunofluorescent-type assays confirms the reliability of ELISA assay and may allow further distinctions between UC and PSC.

EXAMPLE XI

ANCA IN PEDIATRIC ULCERATIVE COLITIS

In the pediatric population, distinguishing between UC, Crohn's disease (CD) and allergic colitis in children with rectal bleeding (RB) is particularly difficult. Since the occurrence of ANCA in adult patients with UC has been well established, studies were undertaken to determine the relationship between the occurrence of ANCA and pediatric UC. To determine whether the presence of ANCA, as measured by DNAase-treated fixed-neutrophil ELISA is sensitive and specific for pediatric UC, serum from children with UC (mean age=13), CD (mean age=14), RB (mean age=3) and other gastrointestinal inflammatory disorders (mean age=8) were tested in a blinded fashion. All ELISA positive samples were examined using immunofluorescence assay described above to determine ANCA staining patterns. ANCA was expressed as a percentage of UC positive sera binding and defined as positive when the value exceeded 2 standard deviations above the mean for normal control sera (≧)12%. The results are presented in Table I.

TABLE I

ANCA IN PEDIATRIC ULCERATIVE COLITIS

| | #Patients | #ANCA+ (%) | MEAN % Positive Cont. | | MEAN Reciprocal Titer | |
|---|---|---|---|---|---|---|
| | | | Total | ANCA+ | Total | ANCA+ |
| UC | 29 | 21 (72) | 44 | 57 | 527 | 705 |
| CD | 41 | 7 (17) | 8 | 16 | 61 | 114 |
| RB | 13 | 3 (23) | 8 | 17 | 87 | 208 |
| Non-IBD | 94 | 7 (7) | 6 | 21 | 63 | 229 |

UC = ulcerative colitis
CD = Crohn's disease
RB = rectal bleeding

Seventy-two percent of children with UC were ANCA positive compared to 17% with CD, 23% with RB and 7% with other gastrointestinal inflammatory disorders (Table 1). The mean percent of positive control at 1:100 dilution was also significantly higher in UC ($p<0.00$ vs CD and non-IBD, $p<0.0$ vs RB). In addition, mean titers of ANCA positive samples were significantly higher, making ELISA titer very specific for UC. The presence of a perinuclear immunofluorescence pattern correlated with titer. It is therefore seen that ANCA is sensitive (72%) and specific (89%) for UC versus other inflammatory disorders.

EXAMPLE XII

ANTIGEN REACTIVE WITH p-ANCA OF UC AND PSC IS TRITON X-100™ INSOLUBLE

1. Count cells in suspension of step 7 of Example II using a microscope and hemacytometer and re-suspend cells in sufficient volume of phosphate buffered saline containing 1.0% Triton X-100™ to acheive $2.5 \times 10^6$ cells per ml phosphate buffered saline containing 0.5% Triton X-100™. Allow to incubate on ice for about 10 minutes.

2. Cytocentrifuge onto glass slide as described in Example III, step 2.

3. Fix cytocentrifuged Triton X-100-™ extract in accordance with the procedure set forth in Example III, step 3.

4. Add 0.05 ml of a 1:20 dilution of UC p-ANCA positive serum or PSC p-ANCA positive serum in phosphate buffered saline to slides. Add 0.05 ml phosphate buffered saline to clean slides as blanks. Incubate for 30 minutes to one hour at room temperature in sufficient humidity to minimize volume loss.

5. Process slides in accordance with the immunofluorescence assay of Example V, steps 2–5.

After Triton X-100™, neutrophil morphology was clearly lost with no evidence of a clear nuclear structure upon reaction with anti-DNA serum. However, cellular DNA was not lost during Triton X-100™ treatment. Both UC p-ANCA positive sera and PSC p-ANCA positive sera showed strong reactivity with fixed Triton X-100™ neutrophil extract. Based upon Triton X-100™ insolubility, an enriched fraction of UC and PSC p-ANCA antigens can be prepared to isolate the antigens.

Although the invention has been described with reference to presently preferred embodiments, it should be understood that various modifications can be made without departing from the spirit of the invention.

We claim:

1. A method of measuring the presence or absence of perinuclear anti-neutrophil cytoplasmic antibodies (p-ANCA) of ulcerative colitis or primary sclerosing cholangitis in a sample, said method comprising:

(a) contacting the sample and a detectable secondary antibody with alcohol-fixed neutrophils under conditions suitable to form a detetable complex of neutrophils, p-ANCA and detectable secondary antibody, wherein said fixed neutrophils are subjected to DNAase under conditions sufficient to cause substantially complete digestion of cellular DNA without significant loss of nuclear or cellular morphology prior to said contacting step, and wherein said secondary antibody has specificity for p-ANCA or the class determining portion of p-ANCA;

(b) separating unbound secondary antibody from the complex;

(c) assaying for the presence, absence or pattern of detectable p-ANCA containing complex by measuring the presence, absence or pattern of complexed secondary antibody, compared to a control, wherein said control is the result of repeating the present method on a sample from the same source, except that the neutrophils of step (a) are not subjected to DNAase.

2. A method according to claim 1, wherein the conditions sufficient to cause substantially complete digestion of cellular DNA, without substantial loss of nuclear or cellular morphology, comprise incubating said neutrophils in a concentration of DNAase of about 2 to 10 units of DNAase per milliliter of buffer for a time in the range of about 15 minutes to one hour at a temperature in the range of about 22° C. to 40° C.

3. A method according to claim 1, wherein the sample and the secondary antibody are sequentially contacted with fixed neutrophils of step (a).

4. A method according to claim 1, wherein the sample and the secondary antibody are simultaneously contacted with fixed neutrophils of step (a).

5. A method according to claim 1, wherein the secondary antibody is anti-IgG.

6. A method according to claim 1, wherein the neutrophils are human neutrophils, the sample is human blood serum and the secondary antibody is anti-human IgG.

7. A method according to claim 1, wherein the secondary antibody is a combination of antibodies, wherein at least one secondary antibody has specificity for the class determining portion of p-ANCA and at least one secondary antibody is detectable.

8. A method according to claim 7, wherein the neutrophils are human neutrophils, the sample is human blood serum, one of the secondary antibodies is mouse anti-human IgG and one of the secondary antibodies is detectable goat anti-mouse IgG.

9. A method according to claim 1, wherein the secondary antibody is detectable by detecting enzymatic conversion, radioactivity, fluorescence or color.

10. A method according to claim 9, wherein the secondary antibody is chemically linked to an enzyme.

11. A method according to claim 10, wherein the enzyme is alkaline phosphatase and the substrate for enzymatic conversion is para-nitrophenyl phosphate.

12. A method according to claim 9, wherein the secondary antibody is chemically linked to a fluorogenic substance.

13. A method according to claim 12, wherein the fluorogenic substance is fluorescein isothiocyanate.

14. A method according to claim 1, wherein the alcohol-fixed neutrophils are methanol-fixed neutrophils.

15. A method of differentiating the conditions of ulcerative colitis without primary sclerosing cholangitis from primary sclerosing cholangitis with or without concomitant ulcerative colitis, and from Crohn's disease, said method comprising:
(a) contacting alcohol-fixed human neutrophils with DNAase under conditions sufficient to cause substantially complete digestion of cellular DNA without significant loss of nuclear or cellular morphology;
(b) contacting the DNAase treated neutrophils of step (a) with blood serum from a patient under conditions suitable to form a complex of neutrophil and p-ANCA;
(c) contacting the complex formed in step (b) with a detectable secondary antibody under conditions suitable to form a detectable complex comprising p-ANCA and secondary antibody; and
(d) assaying for the presence or absence of a detectable complex compared to a control,
wherein said control is the result of repeating the steps (b)–(d) of the present method, except neutrophils employed in step (b) are not subjected to DNAase treatment and
wherein loss of detectable complex associated with perinuclear staining pattern, as compared to said control, indicates ulcerative colitis without primary sclerosing cholangitis,
conversion of detectable complex associated with perinuclear staining pattern to cytoplasmic staining pattern, as compared to said control, indicates primary sclerosing cholangitis without ulcerative colitis or primary sclerosing cholangitis with concomitant ulcerative colitis, and
absence of a detectable complex associated with perinuclear staining pattern in said control indicates Crohn's disease.

16. A method according to claim 15, wherein human neutrophils are contacted with about 2 to 10 units of DNAase per milliliter of buffer for a time in the range of about 15 minutes to one hour at a temperature in the range of about 22° C. to 40° C. and said detectable secondary antibody is anti-human IgG bonded to fluorescein isothiocyanate.

17. A method according to claim 15, wherein human neutrophils are contacted with 3 units of DNAase per milliliter buffer for 30 minutes at 37° C., and said detectable secondary antibody is anti-human IgG bonded to alkaline phosphatase.

18. A method according to claim 1, wherein said neutrophils are immobilized.

19. A method according to claim 18, wherein the sample and the secondary antibody are sequentially contacted with neutrophils of step (a).

20. A method according to claim 18, wherein the sample and the secondary antibody are simultaneously contacted with neutrophils of step (a).

21. A method according to claim 18, wherein the secondary antibody is anti-IgG antibody.

22. A method according to claim 18, wherein the neutrophils are human neutrophils, the sample is human blood serum and the secondary antibody is anti-human IgG antibody.

23. A method according to claim 18, wherein the secondary antibody is a combination of antibodies, wherein at least one secondary antibody has specificity for the class determining portion of p-ANCA and at least one secondary antibody is detectable.

24. A method according to claim 23, wherein the neutrophils are human neutrophils, the sample is human blood serum, one of the secondary antibodies is mouse anti-human IgG antibody and one of the secondary antibodies is detectable goat anti-mouse IgG antibody.

25. A method according to claim 18, wherein the secondary antibody is detectable by detecting enzymatic conversion, radioactivity, fluorescence or color.

26. A method according to claim 25, wherein the secondary antibody is chemically linked to an enzyme.

27. A method according to claim 26, wherein the enzyme is alkaline phosphatase and the substrate for enzymatic conversion is para-nitrophenyl phosphate.

28. A method according to claim 25, wherein the secondary antibody is chemically linked to a fluorogenic substance.

29. A method according to claim 28, wherein the fluorogenic substance is fluorescein isothiocyanate.

30. A method according to claim 15, wherein the alcohol-fixed neutrophils are methanol-fixed neutrophils.

31. A method of detecting the presence of perinuclear anti-neutrophil cytoplasmic antibody (p-ANCA) associated with ulcerative colitis in a sample, comprising:
(a) contacting alcohol-fixed neutrophils with a sample and a detectable secondary antibody under conditions suitable to form a detectable complex of neutrophil, p-ANCA and detectable secondary antibody,
wherein cellular DNA of the alcohol-fixed neutrophils has been digested by DNAase without significant loss of nuclear or cellular morphology, and
wherein the detectable secondary antibody is specific for the class determining portion of p-ANCA;
(b) separating unbound secondary antibody from the complex; and
(c) detecting a staining pattern of the detectable complex as compared to a control,
wherein the control is the result of repeating the present method using alcohol-fixed neutrophils wherein the cellular DNA of the alcohol-fixed neutrophils has not been digested by DNAase, and
wherein the loss of a perinuclear staining pattern, as compared to the control, indicates the presence in the sample of P-ANCA associated with ulcerative colitis.

32. A method according to claim 31, wherein the alcohol-fixed neutrophils are methanol-fixed neutrophils.

33. A method of detecting the presence of perinuclear anti-neutrophil cytoplasmic antibody (p-ANCA) associated with primary sclerosing cholangitis in a sample, comprising:
(a) contacting alcohol-fixed neutrophils with a sample and a detectable secondary antibody under conditions suitable to form a detectable complex of neutrophil, p-ANCA and detectable secondary antibody,
wherein cellular DNA of the alcohol-fixed neutrophils has been digested by DNAase without significant loss of nuclear or cellular morphology, and wherein the detectable secondary antibody is specific for the class determining portion of p-ANCA;

(b) separating unbound secondary antibody from the complex; and (c) detecting a staining pattern of the detectable complex in the DNAase-treated neutrophils as compared to a control, wherein the control is the result of repeating the present method using alcohol-fixed neutrophils wherein the cellular DNA of the alcohol-fixed neutrophils has not been digested by DNAase, and wherein the presence of a cytoplasmic staining pattern in the DNAase-treated neutrophils, and a perinuclear staining pattern in the control, indicates the presence in the sample of P-ANCA associated with primary sclerosing cholangitis.

34. A method according to claim 33, wherein the alcohol-fixed neutrophils are methanol-fixed neutrophils.

35. A method of differentiating the conditions of ulcerative colitis without primary sclerosing cholangitis from primary sclerosing cholangitis with or without concomitant ulcerative colitis, comprising:

(a) contacting alcohol-fixed neutrophils with DNAase under conditions sufficient to cause substantially complete digestion of cellular DNA without significant loss of nuclear or cellular morphology;

(b) contacting a sample from a patient and a detectable secondary antibody with the alcohol-fixed, DNAase-treated neutrophils, under conditions suitable to form a detectable complex of neutrophil(s), p-ANCA and detectable secondary antibody, wherein the detectable secondary antibody has specificity for the class determining portion of p-ANCA; and (c) detecting a staining pattern of the detectable complex in the DNAase-treated neutrophils, as compared to a control, wherein the control is the result of repeating steps (b) and (c) of the present method with alcohol-fixed neutrophil that has not been subjected to step (a) of the present method, wherein the loss of a perinuclear staining pattern as compared to the control indicates ulcerative colitis without primary sclerosing cholangitis, and wherein the presence of a cytoplasmic staining pattern in the CDNAase-treated neutrophils and a perinuclear staining pattern in the control indicates primary sclerosing cholangitis without ulcerative colitis or primary sclerosing cholangitis with concomitant ulcerative colitis.

36. A method according to claim 35, wherein the alcohol-fixed neutrophils are methanol-fixed neutrophils.

37. A kit for measuring the presence or absence of perinuclear anti-neutrophil cytoplasmic antibody of ulcerative colitis or primary sclerosing scholangitis in a sample comprising neutrophils and purified DNAase, wherein said neutrophils are alcohol-fixed.

38. The kit of claim 37, wherein said neutrophils are immobilized.

39. The kit of claim 38, wherein the neutrophils are immobilized on a solid substrate selected from the group consisting of microtiter plates, beads, and glass slides.

40. The kit according to claim 37, further comprising a detectable secondary antibody having specificity for the class determining portion of p-ANCA.

41. A kit for measuring the presence or absence of perinuclear anti-neutrophil cytoplasmic antibody of ulcerative colitis or primary sclerosing cholangitis in a sample, comprising neutrophils, DNAase-treated neutrophils, and a detectable secondary antibody having specificity for the class determining portion of p-ANCAase of ulcerative colitis, wherein said neutrpohils are alcohol-fixed.

42. The kit of claim 41, wherein said secondary antibody is anti-IgG.

43. The kit of claim 41, wherein said neutrophils are immobilized.

44. The kit of claim 43, wherein said neutrophils are immobilized on a solid substrate selected from the group consisting of microtiter plates, beads, and glass slides.

* * * * *

UNITED STATES PATENT AND TRADEMARK OFFICE
CERTIFICATE OF CORRECTION

PATENT NO.     : 5,750,355
DATED          : May 12, 1998
INVENTOR(S)    : Targan et al.

It is certified that error appears in the above-identified patent and that said Letters Patent is hereby corrected as shown below:

Column 1,
Line 28, please delete "IED are" and replace with -- IBD are --.

Column 9,
Line 63, please delete "IgGo-FITC" and replace with -- IgG($\mu$)-FITC --.

Column 13,
Line 22, please delete "p<0.0 vs RB)." and replace with -- p<0.01 vs RB). --.

Column 14, claim 1,
Line 21, please delete "detetable" and replace with -- detectable --.

Column 18, claim 37,
Line 15, please delete "scholangitis" and replace with cholangitis --.

Column 18, claim 41,
Line 31, please delete "p-ANCAse" and replace with -- p-ANCA --.

Signed and Sealed this

Twenty-sixth Day of February, 2002

*Attest:*

JAMES E. ROGAN
*Attesting Officer*    *Director of the United States Patent and Trademark Office*